US00PP36628P2

(12) United States Plant Patent
de Vallois

(10) Patent No.: US PP36,628 P2
(45) Date of Patent: Apr. 22, 2025

(54) ***RHAPHIDOPHORA* PLANT NAMED 'TUXRAP1'**

(50) Latin Name: *Rhaphidophora decursiva*
Varietal Denomination: TUXRAP1

(71) Applicant: Antoine de Vallois, South Miami, FL (US)

(72) Inventor: Antoine de Vallois, South Miami, FL (US)

(73) Assignee: Florida Tuxedo Plants, Inc., Miami, FL (US)

( * ) Notice: Subject to any disclaimer, the term of this patent is extended or adjusted under 35 U.S.C. 154(b) by 0 days.

(21) Appl. No.: 18/937,969

(22) Filed: Nov. 5, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Zachariah Allan Kay
(74) *Attorney, Agent, or Firm* — James R. Holm; Plant Novelty Rights, LLC

(57) ABSTRACT

A new and distinct *Rhaphidophora* plant named 'TUXRAP1' particularly distinguished by its unique and uniformly mottled leaf variegation pattern colored yellowish grey.

6 Drawing Sheets

Genus and species: *Rhaphidophora decursiva.*
Variety denomination: 'TUXRAP1'.

BACKGROUND OF THE NEW PLANT

The present invention comprises a new and distinct variety of *Rhaphidophora* plant, botanically known as *Rhaphidophora decursiva*, and hereinafter referred to by its name 'TUXRAP1'. The genus *Rhaphidophora* is closely related to the genera *Philodendron* and *Monstera. Rhaphidophora* are tropical climbing plants native to Southeast Asia.

The new *Rhaphidophora* cultivar 'TUXRAP1' is a naturally-occurring, whole plant mutation discovered by the inventor in a cultivated population of unnamed commercially grown *Rhaphidophora decursiva* plants (unpatented). The new *Rhaphidophora* cultivar 'TUXRAP1' was discovered in September 2021 by the inventor in a commercial shade house located in Miami, Florida. The inventor selected 'TUXRAP1' as a single plant within a large population of cultivated *Rhaphidophora* plants due to its unique variegated foliage pattern.

Plants of the new *Rhaphidophora* cultivar 'TUXRAP1' and plants of the unnamed commercial and parent *Rhaphidophora* cultivar differ in that the parent cultivar has solid green leaves, whereas 'TUXRAP1' has variegated leaves. Asexual reproduction of 'TUXRAP1' by vegetative stem divisions was first performed in October 2021 in Miami, Florida. Asexual reproduction of the new *Rhaphidophora* cultivar 'TUXRAP1' has shown that the unique features are stable and reproduced true-to-type through 10 successive generations.

Plant Breeder's Rights for this variety have not been applied for. 'TUXRAP1' has not been made publicly available or sold anywhere in the world more than one year prior to the effective filing date of this application.

SUMMARY OF THE INVENTION

The new *Rhaphidophora* cultivar has not been observed under all possible environmental conditions. The phenotype may vary somewhat with variations in environment such as temperature, day length, light intensity, water status, fertilizer rate and type, without, however, any variance in genotype.

The most outstanding and distinguishing characteristic of the new *Rhaphidophora* plant 'TUXRAP1' is its unique and uniformly mottled leaf variegation pattern colored yellowish grey. This unique feature distinguishes 'TUXRAP1' as a new and distinct variety of *Rhaphidophora decursiva.*

DESCRIPTION OF THE FIGURES

This new *Rhaphidophora* cultivar 'TUXRAP1' is illustrated by the accompanying-colored photographs which show the overall appearance and distinct characteristics of the plant. The colors shown are as true as can be reasonably obtained by conventional photographic procedures. The photographs are of a 1-year-old plant grown in a 3-gallon container in a commercial shade house in Miami, Florida under 73 percent light exclusion. Colors in the photographs may differ slightly from the color values cited in the botanical description which accurately describes the colors of the new variety.

DESCRIPTION OF THE NEW VARIETY

Figure 1:
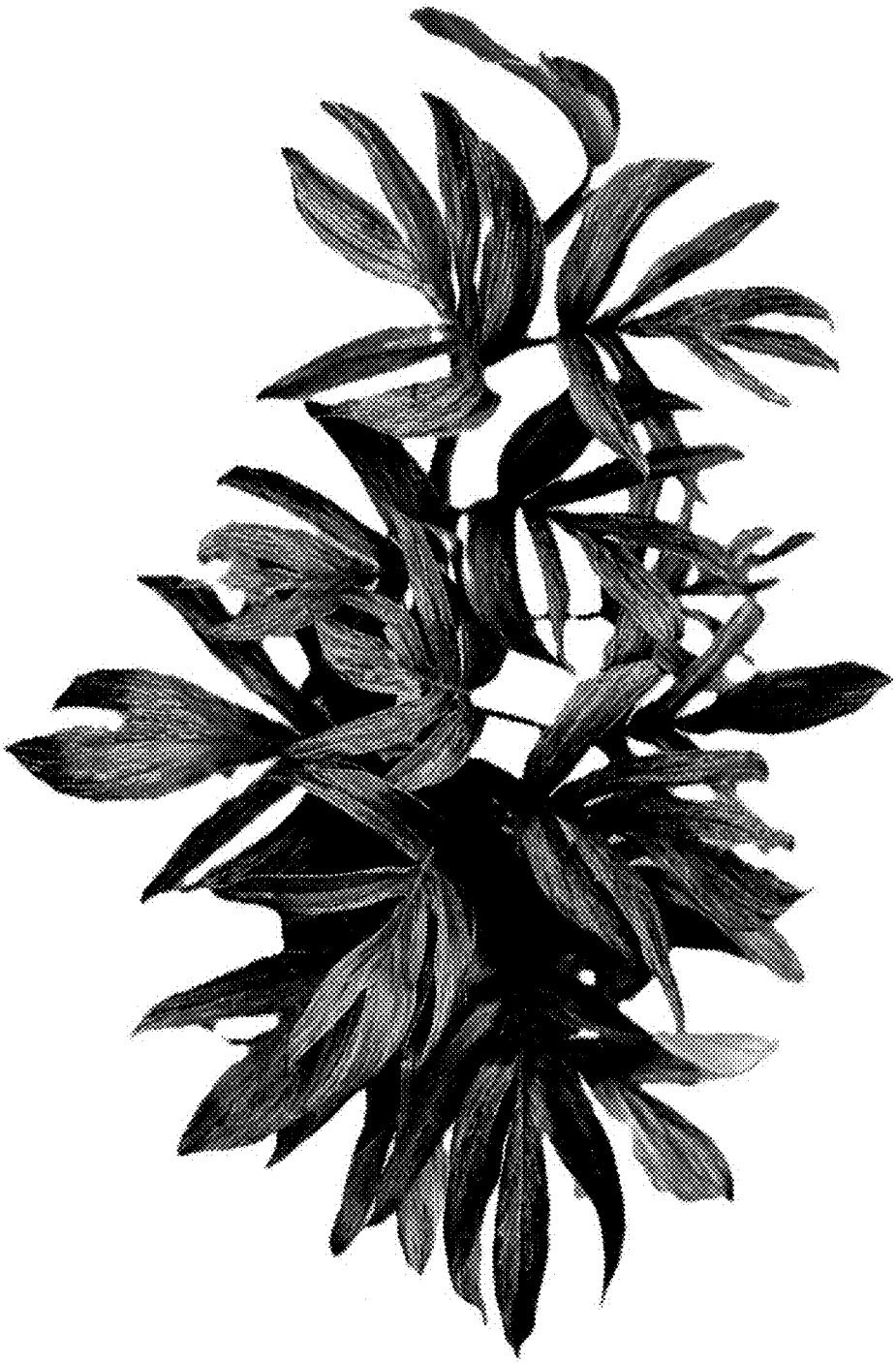
FIG. 1 shows an overhead view of the overall plant form and foliage of 'TUXRAP1'.
Figure 2:
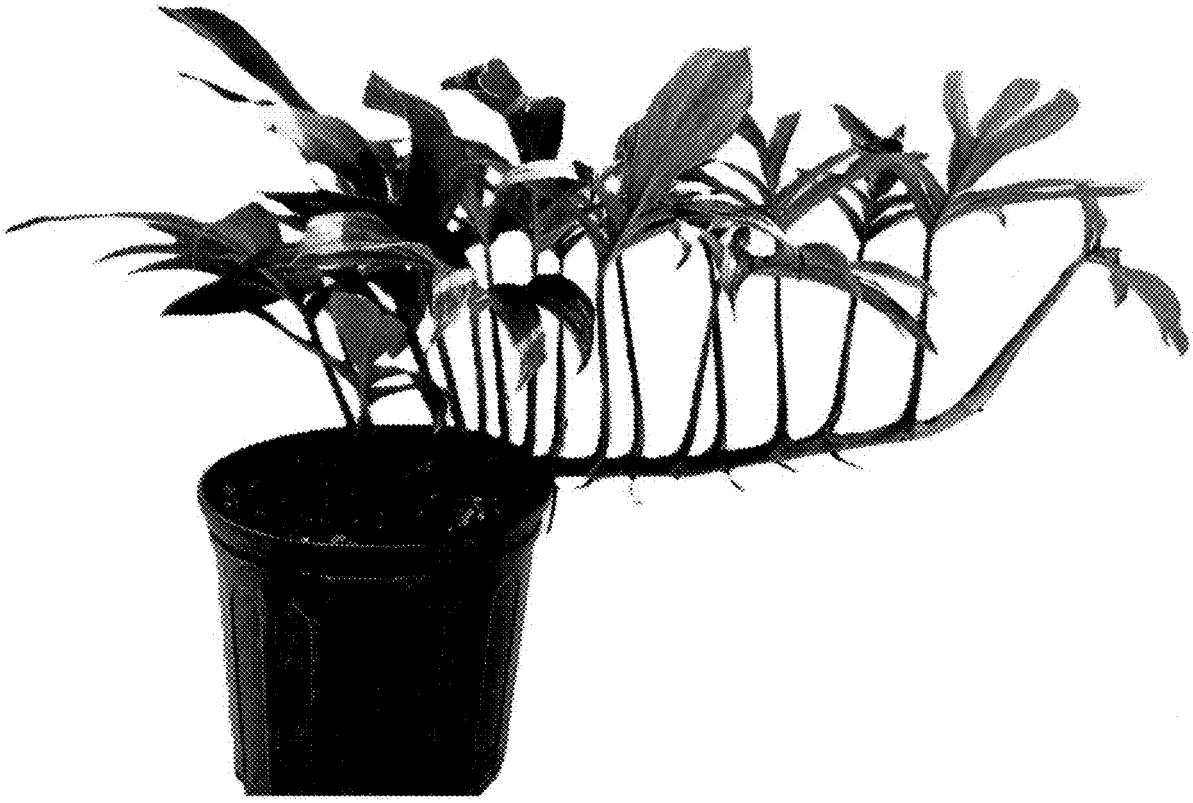
FIG. 2 shows a sideview of the overall plant form and foliage of 'TUXRAP1'.
Figure 3:
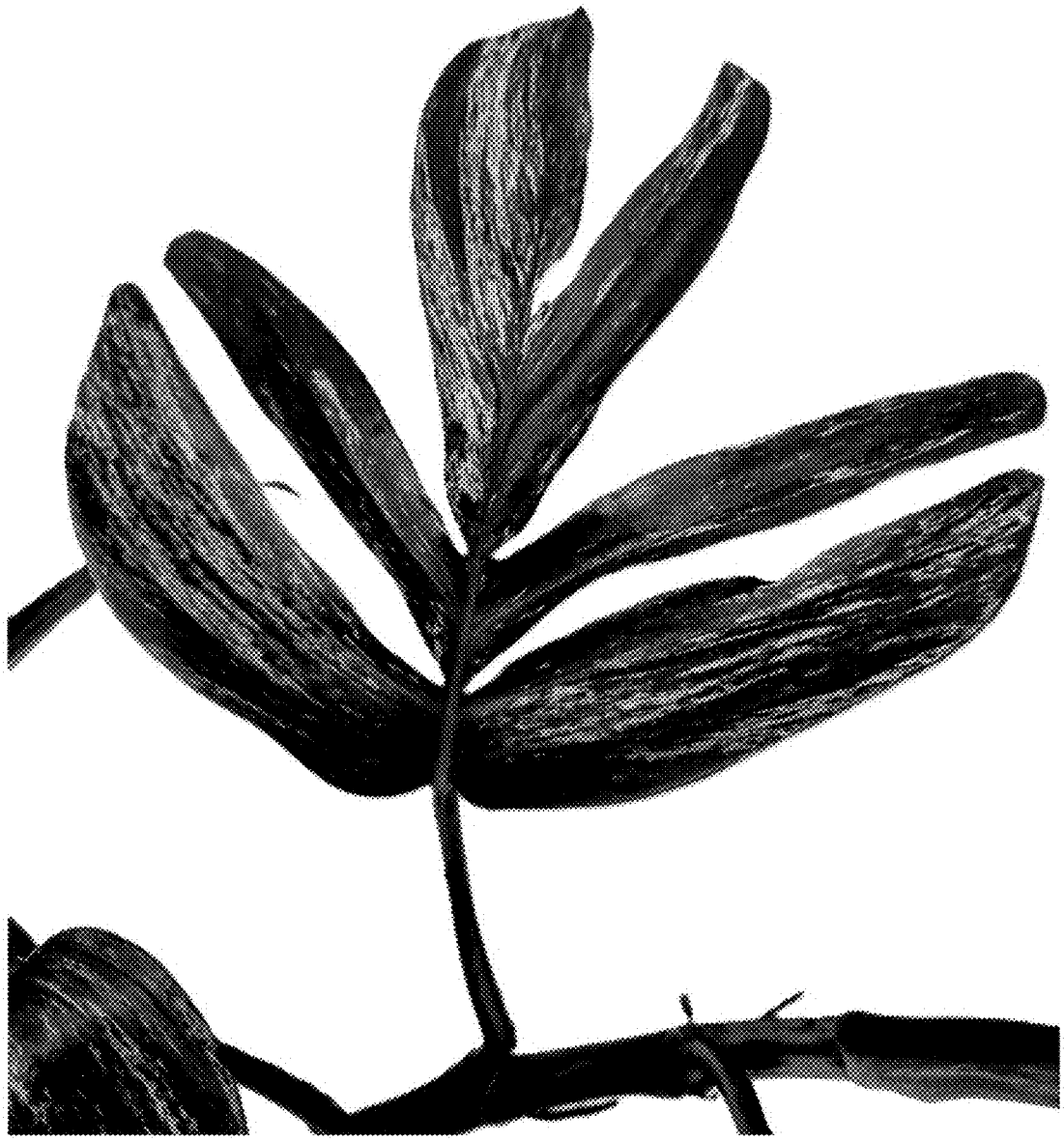
FIG. 3 shows a closeup view of the adaxial surface of a typical mature leaf of 'TUXRAP1'.
Figure 4:
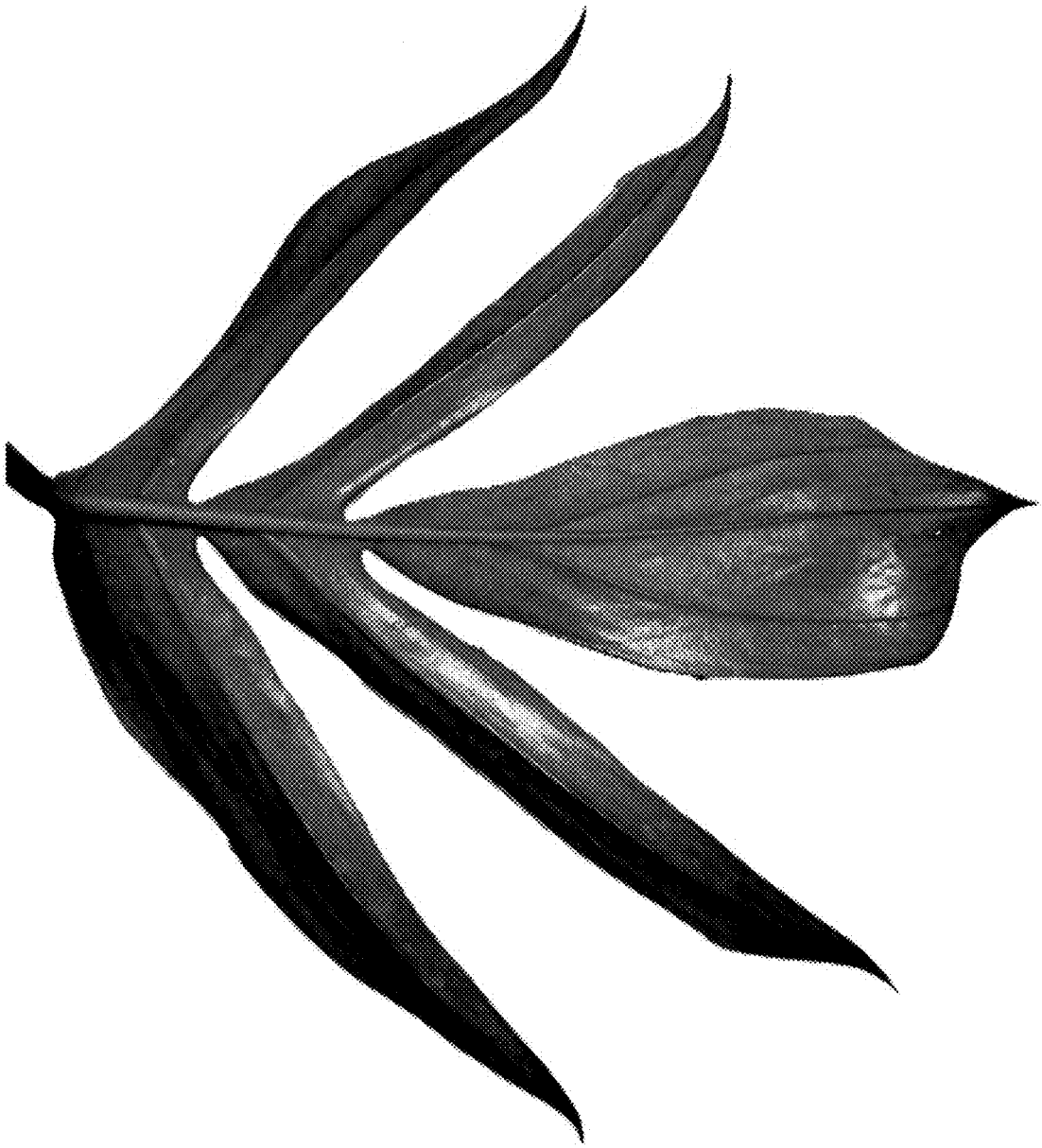
FIG. 4 shows a closeup view of the abaxial surface of a typical mature leaf of 'TUXRAP1'.
Figure 5:
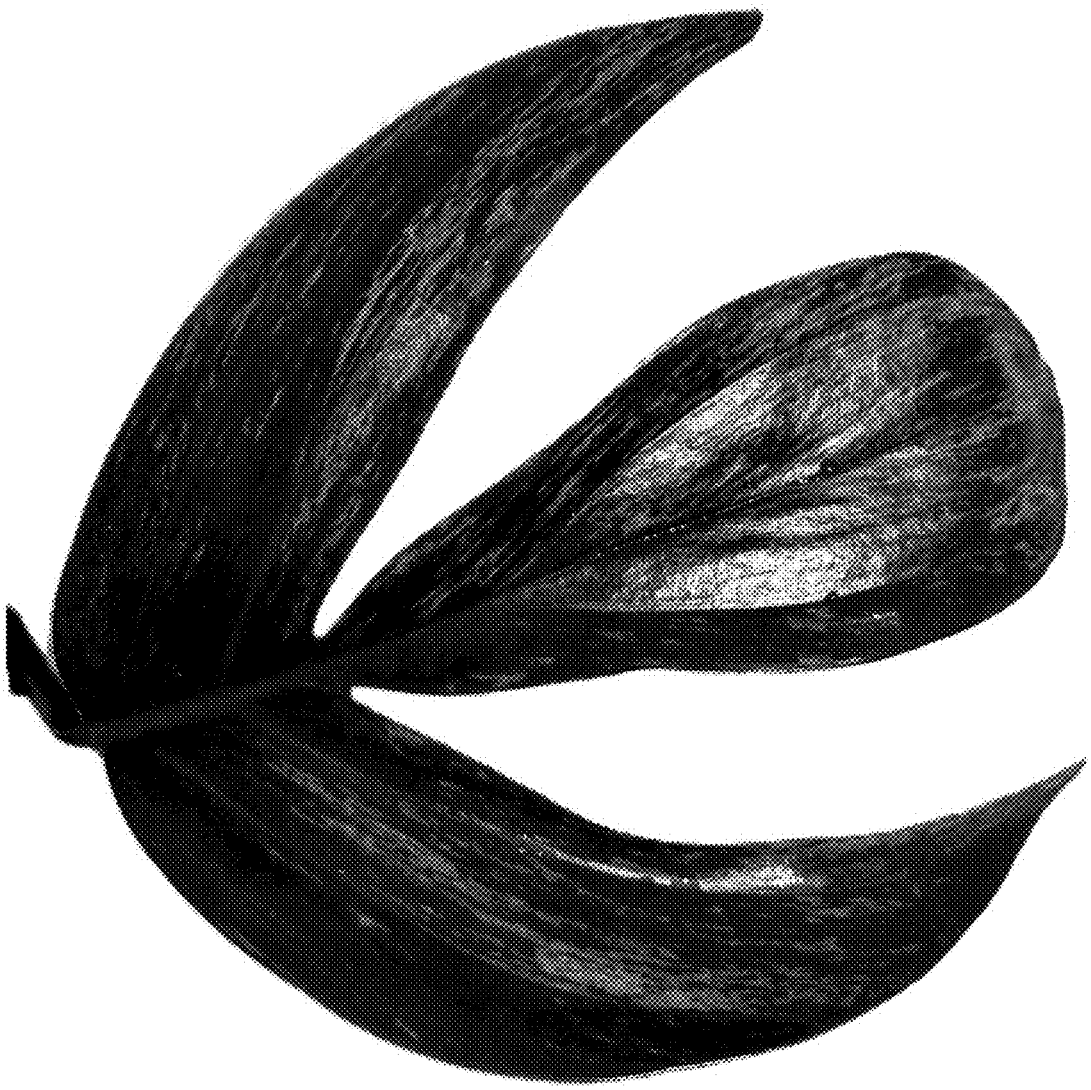
FIG. 5 shows a closeup view of the adaxial surface of a typical immature leaf of 'TUXRAP1'.
Figure 6:
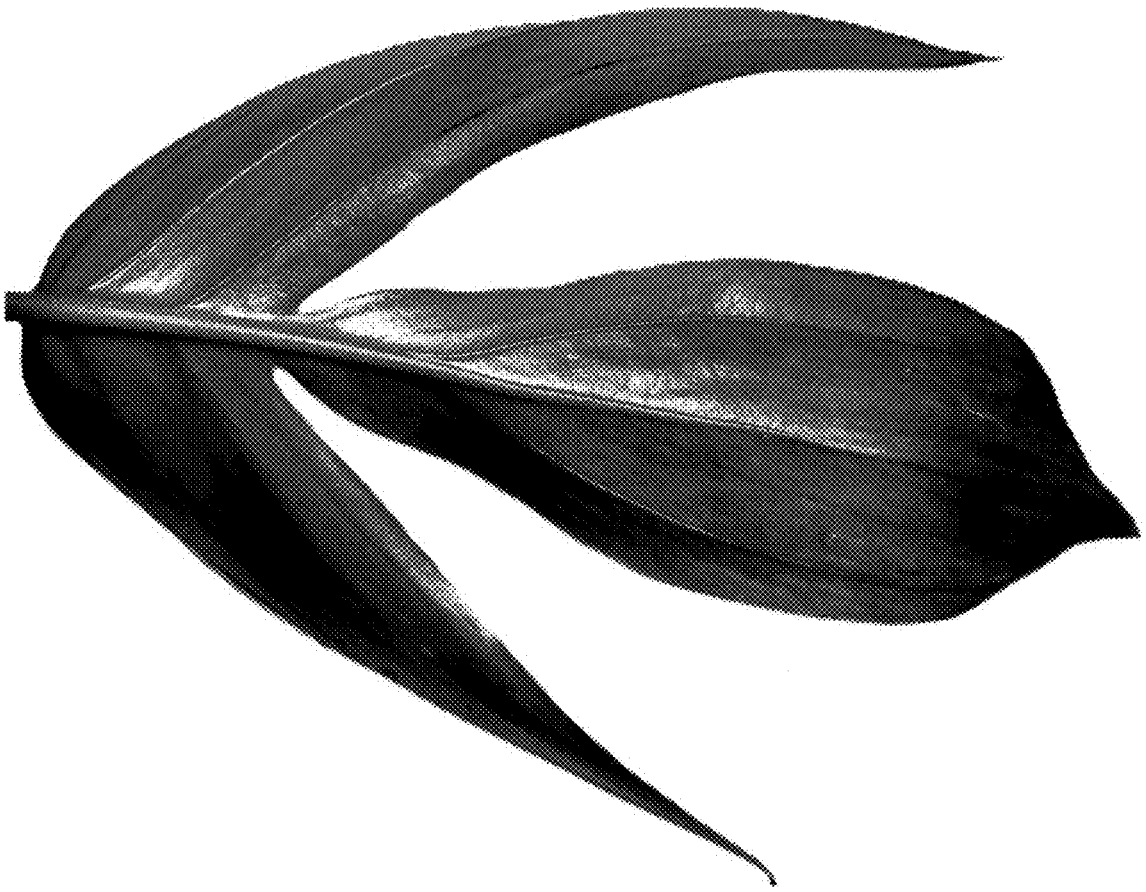
FIG. 6 shows a closeup view of the abaxial surface of a typical immature leaf of 'TUXRAP1'.

In the following description, color references are made to The Royal Horticultural Society Colour Chart, Sixth Edition, except where general color terms of ordinary dictionary significance are used.

The following observations and measurements describe plants grown in a commercial shade house in Miami, Florida under 73 percent light exclusion. Detailed descriptions were taken in September 2024 from 1-year-old plants grown in 3-gallon containers. Measurements and numerical values represent averages of typical plant types.

DETAILED BOTANICAL DESCRIPTION

Classification:

*Family*.—Araceae.

*Botanical*.—*Rhaphidophora decursiva*.

*Common*.—Dragon tail plant.

*Denomination*.—'TUXRAP1'.

General description:

*Plant type*.—Tropical perennial.

*Growth habit*.—Prostrate when grown in containers without artificial support but can be trained to grow vertically with artificial support.

*Growth rate*.—Growth rate depends on time of year and light intensity, but generally 2-inches of stem growth per month during the winter months in south Florida and 4-inches of stem growth during the summer months in south Florida.

*Propagation type*.—Vegetative stem divisions.

*Time to initiate roots*.—2 weeks during summer months.

*Time to produce a rooted young plant*.—4 weeks during summer months.

*Roots*.—Thick, white fleshy roots with fine lateral roots.

Stems:

*Branching characteristics*.—Monopodial with one dominant central stem, rarely branches under cultivation.

*Aspect*.—Rounded.

*Length*.—47.0 cm.

*Width*.—2.0 cm at the proximal end, tapering to 1.5 cm at the distal end.

*Internode length*.—Average 4.6 cm.

*Strength*.—Rigid and strong.

*Texture and luster*.—Smooth and shiny.

*Color*.—Main color is NN137A (greyish olive green) with faint linear striations colored 145A (strong yellow green), striations are more visible towards the distal (younger) end of the stem.

Foliage:

*Quantity of leaves per plant*.—Average 16 on a 1-year-old stem.

*Arrangement*.—Alternate.

*Attachment*.—Petiolate.

*Lamina*.—Shape: Pedate, deeply incised. Number of incisions: 4 to 5. Length: Approximately 20.5 cm. Width: Approximately 20.0 cm at the widest point above the base of the lamina. Orientation: Horizontal to moderately arched upwards. Aspect: Convex. Apex: Obtuse, but often moderately incised on mature leaves. Base: Slightly to moderately cordate and sometimes truncate. Margins: Deeply incised with course undulation. Texture and luster, adaxial surface: Moderately rugose, shiny on juvenile leaves and becoming more matte on mature leaves. Texture and luster, abaxial surface: Glabrous and matte. Midrib: Recessed on the upper surface and protruding on the lower surface. Venation pattern: Pinnate, veins are recessed on the upper surface and protruding on the lower surface. Color: Juvenile foliage, adaxial surface: Main color is 137A to 137B (moderate olive green) with mottled variegation colored 145C (light yellow green). Juvenile foliage, abaxial surface: 148C to 148D (greyish yellow green). Mature foliage, adaxial surface: Main color is NN137A (greyish olive green) with mottled variegation colored 194B to 194C (yellowish grey). Mature foliage, abaxial surface: N148A (moderate yellow green).

*Petioles*.—General description: Distal end is rounded, proximal end is sheathed and slightly winged and shallowly recessed between the wings. Sheath: Translucent and glossy on young foliage colored 143C (strong yellow green) with streaks of 145D (light yellow green), sheathing remains attached on older petioles but becomes brown and desiccated with age. Strength: Moderately strong. Orientation: Upright and straight. Length: Approximately 16.4 cm to 17.5 cm. Width: Approximately 1.5 to 2.0 cm at the point of attachment to the main stem and tapering to 0.6 cm at the base of the lamina. Texture and luster: Glabrous and matte. Color: Outer surface: 137A to 137B (moderate olive green). Lower inner surface (between the wings): 195D (pale yellow green) on young petioles with speckling of 147B (moderate yellow green), darkening to 137A (moderate olive green) on older petioles.

Inflorescence: None observed to date.

Cold tolerance: Can tolerate down to 50 degrees Fahrenheit, otherwise not cold hardy.

Disease and pest tolerance: None observed to date.

Drought tolerance: Moderately tolerant.

COMPARISON WITH PARENT AND COMMERICAL VARIETY

'TUXRAP1' differs from the unnamed parent and commercial *Rhaphidophora* plant in that 'TUXRAP1' has leaves with mottled variegation, whereas leaves of the parent and commercial plant are solid green with no variegation.

What is claimed is:

1. A new and distinct variety of *Rhaphidophora* plant named 'TUXRAP1', substantially as illustrated and described herein.

* * * * *